United States Patent [19]

Yamaguchi et al.

[11] 4,440,858

[45] Apr. 3, 1984

[54] PROCESS FOR THE CONTINUOUS PRODUCTION OF ACRYLAMIDE OR METHACRYLAMIDE USING MICROORGANISMS

[75] Inventors: Yasumasa Yamaguchi; Ichiro Watanabe; Yoshiaki Satoh, all of Kanagawa, Japan

[73] Assignee: Nitto Chemical Industry Co., Ltd., Tokyo, Japan

[21] Appl. No.: 146,937

[22] Filed: May 2, 1980

[30] Foreign Application Priority Data

May 2, 1979 [JP] Japan ................... 54-53380

[51] Int. Cl.³ ............. C12P 13/02; C12N 11/00; C12N 11/02; C12N 11/04; C12R 1/01; C12R 1/07; C12R 1/13; C12R 1/15; C12R 1/265; C12R 1/365
[52] U.S. Cl. ......................... 435/129; 435/174; 435/177; 435/182; 435/832; 435/822; 435/840; 435/843; 435/859; 435/872
[58] Field of Search ............ 435/129, 177, 182, 244, 435/813, 819, 822, 832, 840, 843, 859, 872, 174

[56] References Cited

U.S. PATENT DOCUMENTS 4,001,081 1/1977 Commeyras et al. ............. 435/129
4,248,968 2/1981 Watanabe et al. ............... 435/129

OTHER PUBLICATIONS

Vieth et al., *Applied Biochemistry and Bioengineering,* vol. 1, Academic Press, New York, 228–229 (1976).
Brodelius, *Advances in Biochemical Engineering,* vol. 10, Springer-Verlag, New York, 75, 84, 85 (1978).

*Primary Examiner*—Esther M. Kepplinger
*Attorney, Agent, or Firm*—Sughrue, Mion, Zinn, Macpeak & Seas

[57] ABSTRACT

A process for the continuous production of acrylamide or methacrylamide from acrylonitrile or methacrylonitrile by use of a microorganism capable of promoting the hydration of acrylonitrile or methacrylonitrile into the corresponding amide.

Said process comprising immobilizing the microorganism or enzyme extracted therefrom, continuously bringing the acrylonitrile or methacrylonitrile into contact with the immobilized microorganism or enzyme in at least one reactor containing an aqueous medium at a pH pf 6 to 10 to cause the hydration reaction, and recycling a part of the reacted solution to dilute the unreacted acrylonitrile or methacrylonitrile and water therewith.

14 Claims, No Drawings

PROCESS FOR THE CONTINUOUS PRODUCTION OF ACRYLAMIDE OR METHACRYLAMIDE USING MICROORGANISMS

BACKGROUND OF THE INVENTION

This invention relates to a process for continuously producing acrylamide or methacrylamide from acrylonitrile or methacrylonitrile by use of microorganisms.

A process for producing acrylamide or methacrylamide (hereinafter both referred to simply as "(meth)acrylamide") by reacting acrylonitrile or methacrylonitrile (hereinafter both referred to simply as "(meth)acrylonitrile") with water in the presence of a copper-based catalyst has hitherto been known, but this process has disadvantages in that the preparation of the copper-based catalyst is complex, the reproduction of the catalyst is difficult, and the separation and purification of the (meth)acrylamide formed is complicated. It has therefore been desired to develop improved processes which can be used advantageously from a commercial standpoint.

Recently, U.S. Pat. No. 4,001,081 has disclosed a process for the biological production of (meth)acrylamide from (meth)acrylonitrile using microorganisms belonging to the genera Bacillus, Bacteridium in the sense of Prévot, Micrococcus and Brevibacterium in the sense of Bergey.

Another process proposed for the production of (meth)acrylamide from (meth)acrylonitrile using microorganisms belonging to the genera Corinebacterium and Nocardia is described in Japanese Patent Application (OPI) No. 129190/79 (the term "OPI"0 as used herein refers to a "published unexamined Japanese patent application").

The microorganisms disclosed in both U.S. Pat. No. 4,001,081 and Japanese Patent Application (OPI) No. 129190/79 exhibit high initial activity for the hydration reaction. However, because of their quick reduction in activity under ordinary reaction conditions, their useful lives are short. Therefore such microorganisms have not been able to effect a sufficient increase in the accumulated concentration of (meth)acrylamide, and the repeated use of the microorganisms has been almost impossible. Furthermore, since the microorganisms are of very small size, if they are used in their natural state, it is difficult to remove them from the aqueous solution of (meth)acrylamide formed and the aqueous solution of (meth)acrylamide separated from the microorganisms is discolored, causing obvious problems when used in the production of polymers.

SUMMARY OF THE INVENTION

As a result of extensive and elaborated investigations to solve the above-described defects, particularly with respect to enzyme activity, it has now been found that the enzyme activity (that is, the reaction velocity ($\mu$mol/min) per mg dried sample) of a microorganism in (meth)acrylonitrile and water mixture decreases quickly with increasing concentration of the (meth)acrylonitrile therein, whereas, in contrast thereto, in an aqueous (meth)acrylamide solution the enzyme activity is markedly stable.

Therefore, it has now been found that the various problems as described above can be solved by reacting (meth)acrylonitrile and water in an aqueous medium while diluting the reactants with a part of the aqueous solution (meth)acrylamide formed in the aqueous medium.

This invention, therefore, provides a process for continuously producing (meth)acrylamide from (meth)acrylonitrile by use of a microorganism capable of promoting the hydration reaction of (meth)acrylonitrile into (meth)acrylamide.

Said process comprising immobilizing the microorganism or enzyme extracted therefrom to a substrate, and continuously bringing (meth)acrylonitrile into contact with the immobilized microorganism or enzyme in an aqueous medium to cause the hydration reaction, and recycling a part of the reacted solution to dilute the (meth)acrylonitrile and water therewith.

One feature of this invention is that a (meth)acrylamide aqueous solution of high concentration can be stably obtained without decreasing the enzyme activity over a long period of time.

Another feature is that investments for reactors, coolers, etc., and other costs, such as for microorganisms, immobilizing agents, etc., can be markedly reduced because of the high efficiency of the process of this invention, in which the amount of the microorganism used per unit of product produced is small, and the microorganism itself and impurities eluted therefrom have no substantial effect on the (meth)acrylamide product.

DETAILED DESCRIPTION OF THE INVENTION

Any microorganism capable of hydrolyzing (meth)acrylonitrile to give the corresponding (meth)acrylamide can be used in this invention, irrespective of the group into which it is classified by the taxonomy of microorganisms. For example, those microorganisms belonging to the genera Bacillus, Bacteridium in the sense of Prévot, Micrococcus and Brevibacterium in the sense of Bergey as described in U.S. Pat. No. 4,001,081 and to the genera Corynebacterium and Nocardia as described in Japanese Patent Application (OPI) No. 129190/79 can be used.

Preferred microorganisms include Strain N-771 (deposited in the Fermentation Research Institute, the Agency of Industrial Science and Technology under the accession number of FERM-P No. 4445) and Strain N-774 (FERM-P No. 4446), both belonging to the genus Corynebacterium, and Strain N-775 (FERM-P No. 4447) belonging to the genus Nocardia, as described in Japanese Patent Application (OPI) No. 129190/79.

These microorganisms can be immobilized and used in this invention. For this immobilization any hitherto known procedures can be employed. For example, a method of entrapping or cross-linking can be employed, but the entrapping with polyacrylamide based gel is particularly preferred.

For microorganisms immobilized according to the polyacrylamide based gel entrapping method, the recovery of enzyme activity using such method may be from 30 to 60%. In contrast, microorganisms immobilized according to the polyacrylamide gel entrapping method using in the present invention have the feature that the recovery of activity is almost 100%, attributable to the microorganism being an acrylamide-producing strain which is stable against a high concentrated acrylamide, and effecting the immobilization at a temperature of 15° C. or less.

The immobilization can be carried out as follows: a microorganism as described is dispersed in an aqueous medium (e.g., water, an isotonic sodium chloride solution or a buffer solution), containing an acrylamide based monomer and a cross-linking agent, a polymerization initiator and a polymerization accelerator are added thereto, and the resulting mixture is gelled through polymerization in a temperature range of from about 0° C. to 30° C., and preferably from 0° C. to 15° C. and at a pH of from about 5 to 10, and preferably from 6 to 8.

The microorganism content in the polymerization solution is usually from about 0.1 to 50% by weight, and preferably from 1 to 20% by weight; the desired content varies depending upon the kind of the microorganism and the conditions under which it is used.

Acrylamide based monomers for use in carrying out immobilization according to the invention include acrylamide and methacrylamide. If desired, they can be used in combination with ethylenically unsaturated monomers copolymerizable therewith. The acrylamide based monomer in the reaction solution is used in such a concentration that a gel is formed by the polymerization reaction in the reaction solution. The concentration of the acrylamide based monomer in the polymerization reaction solution is usually from about 2 to 30% by weight, and preferably from 5 to 20% by weight.

Examples of cross-linking agents useful in immobilizing the microorganism or enzyme according to the invention include N,N'-methylenebisacrylamide and 1,3-di(acrylamidomethyl)-2-imidazoline.

As polymerization initiators and polymerization accelerators, compounds are chosen which do not substantially inhibit the activity of the microorganism. Potassium persulfate and ammonium persulfate are generally useful as polymerization initiators, and dimethylaminopropionitrile and triethanolamine can be used as polymerization accelerators. These additives can be used in amounts, for example, of from about 0.01 to 10% by weight, respectively.

When enzyme is to be used according to the invention, an enzyme solution obtained by extration thereof from the microorganism by the supersonic method, the freezemelt method, the lysozyme method, etc., is purified, if necessary and immobilized.

The method of extracting and purifying an enzyme solution from the microorganism obtained by the centrifugation of the culture solution completed can be a known method, e.g, the method comprising suspending the washed microorganisms with a buffer solution having pH suitable for maintaining the stability of the enzyme, treating the suspended microorganisms with a French press or ultrasonic waves to destroy the microorganisms, separating the extract solution (a crude extract of the microorganisms) from the pieces of the crushed microorganisms, resolving the crude extract solution with ammonium sulfate in the known method and then dialyzing the precipitates obtained to prepare a crude enzyme solution, and collecting an active fraction of the crude enzyme solution using a chromatograph such as diethylaminoethyl cellulose, such as Sephadex G-200 (trademark of a product of Pharmacia Co., Sweden) or the like to obtain the partially purified enzyme.

For this immobilization any known immobilization method can be employed. For example, each of the methods of entrapping, cross-linking and carrier-bonding can be employed, but the ion bonding method is preferred in which the enzyme is bonded to and deposited on granular solids of ion exchangers such as a porous anion exchange resin and diethylaminoethyl cellulose.

The immobilized microorganism or enzyme may be in any known form, but preferably is in a particle form.

A fixed bed type, fluidized bed type reactor can be used in this invention, but the fixed bed type reactor is preferred in that the immobilized microorganism or enzyme tends to break down to a lesser extent. Replacement of the immobilized microorganism or enzyme is usually carried out batchwise, and it is to be noted that a moving bed type reactor in which the feed and the discharge are semibatchwise or continuously carried out is contemplated as a type of fixed bed type reactor within the scope of this invention. A floating bed type reactor as described in U.S. Pat. No. 3,288,567 and a spouting bed type reactor are used as a fluidized bed type. Contacting the immobilized microorganism or enzyme with the reaction solution using counter-current or co-current flow techniques is preferred in that these techniques permit a reduction with respect to the amount of the immobilized microorganism or enzyme required to carry out the process.

Usually one or two, or if desired three or more reactors filled with the immobilized microorganism or enzyme are connected in series, in which the reaction is continuously carried out after diluting the (meth)acrylonitrile and water thereinto with a part of the reaction solution which has been withdrawn and recycled, with the remaining reaction solution being withdrawn as a product. That is, a part of the reaction solution is continuously withdrawn as a (meth)acrylamide aqueous solution in a concentration approaching the concentration of (meth)acrylonitrile in the aqueous medium being introduced.

When an apparatus wherein two or more reactors are connected in series is employed, it is also possible to dilute the (meth)acrylonitrile and water used as a starting material by recycling thereinto a part of the effluent reaction solution withdrawn from each reactor in which the (meth)acrylonitrile and water have been introduced. To the reactor(s) other than first reactor, only acrylonitrile is supplied. Furthermore, the (meth)acrylonitrile and water to be diluted include the unreacted (meth)acrylonitrile and water supplied from the preceding reactor, as well as the freshly introduced (meth)acrylonitrile and water.

Separation of the immobilized microorganism or enzyme from the reaction solution is usually effected in the reactor, and immobilized microorganism or enzyme entrained in the reaction solution can be easily separated by filtration and sedimentation.

The concentration of (meth)acrylamide in the reaction solution can be raised to the limit of their individual solubilities. In the case of acrylamide, it is preferably controlled within a concentration of 5 to 25% by weight.

The starting materials, i.e., (meth)acrylonitrile and water, are diluted with previously reacted solution which is recycled. The dilution effect increases with an increase in the dilution ratio, but the range of the dilution ratio is determined according to the dilution effect and fluid resistance. The preferred dilution ratio range is from 2 times to 100 times.

An increment of the dilution ratio to greater than 100 times not only exerts almost no beneficial influence on increasing the life of the immobilized microorganism or enzyme, but also increases the fluid resistance and, as a result, it becomes difficult to increase productivity by increasing the flow rate. On the other hand, in the case of small dilution ratios, such as less than 2, the dilution effect is low and the increase in the life of the immobilized microorganism or enzyme is undesirably small. Although the dilution can be carried out in the reactor, it is preferred to effect the mixing and dilution prior to introducing the (meth)acrylonitrile and water into the reactor.

The reaction is desirably carried out at a temperature of from the freezing point of the reaction system to about 30° C., and preferably from the freezing point of the system to 15° C., which enables the production of a (meth)acrylamide aqueous solution of high concentration over a long period of time. The pH value is desirably maintained from about 6 to 10, and preferably from 7 to 9, which enables the microorganism or enzyme to exhibit a desirable level of (meth)acrylonitrile hydration activity. Furthermore, the conditions tend to prevent the entrainment of impurities and a reduction in yield owing to the formation of by-products such as acrylic acid and methacrylic acid.

The rate of the reaction or conversion can be controlled by the amount of the immobilized microorganism or enzyme, the reaction temperature, the reaction period, the flow rate, and other factors. By choosing suitable conditions for a particular microorganism or enzyme, it is possible to effect the reaction to obtain a yield substantially 100%. An important factor is the space velocity (SV), which is represented by the following equation:

$$SV\,(hr^{-1}) = \frac{\text{the feed rate (volume) per unit of time}}{\text{the volume of the reactor}}$$

The SV of each reactor is from about 0.1 to 20 ($hr^{-1}$), and is preferably from 0.3 to 5. Thus, (1/SV) (hr) shows the contact time between the starting material and the immobilized microorganism or enzyme.

When unreacted (meth)acrylonitrile is present in the reacted solution, the reacted solution can be introduced into another reactor to complete the reaction, or the unreacted (meth)acrylonitrile can be removed by stripping or distillation. The (meth)acrylonitrile and water recovered can be recycled to the hydration reaction. The number of the additional reactors required to react the residual (meth)acrylonitrile present in a slight amount is usually only 1 to 2. In these reactors, since the concentration of (meth)acrylonitrile is low, it is not necessary to further dilute the solutions in said reactors with the reaction product solution.

According to this invention, the life of the immobilized microorganism or enzyme can be outstandingly lengthened and a (meth)acrylamide aqueous solution of high concentration can be stably obtained over a long period of time. The aqueous solution of (meth)acrylamide produced by this invention can be used as is, or after being concentrated by conventional procedures, as a starting material for production of various polymers. Alternatively it can be obtained as crystals by application of procedures such as concentration and cooling. The crystals can be precipitated by increasing the concentration of the (meth)acrylamide to a concentration greater than the solubility limit thereof in a procedure of concentrating, or decreasing the solubility, of the (meth)acrylamide by the procedure of cooling a (meth)acrylamide aqueous solution of high concentration. Where the concentration of (meth)acrylamide in the reaction solution is high, the reaction solution is sometimes slightly colored, but it can be purified by use of a porous anion exchange resin which is strongly basic to weakly basic.

The following examples are given to illustrate this invention in greater detail. The measurement of the reaction product and unreacted starting material was conducted using conventional gas chromatography techniques.

EXAMPLE 1

40 parts of a washed mass (water content 75%) of Strain N-774, which had been prepared by aerobically incubating on a culture medium (pH 7.2) containing 1% of glucose, 0.5% of peptone, 0.3% of yeast extract and 0.3% of malt extract, 4.5 parts of acrylamide, 0.5 part of N,N'-methylenebisacrylamide, and 40 parts of physiological saline were mixed to give a uniform dispersion. To this dispersion, 5 parts of a 5% aqueous solution of dimethylaminopropionitrile and 10 parts of a 2.5% aqueous solution of potassium persulfate were added, and the resulting mixture was polymerized by maintaining at 10° C. for 30 minutes. The thus obtained microorganism-containing gel was pulverized into small particles and fully washed with physiological saline, to give 100 parts of immobilized microorganism gel particles.

A column having an inner diameter of 3 cm and a length of 25 cm, provided with a temperature-control jacket, was charged with 40 g of the microorganism. A feed mixture of 0.075 part of acrylonitrile and 0.925 part of a phosphoric acid buffer aqueous solution (pH 8.0) was, after being mixed with 4 parts of effluent from the bottom of the column (at the start of the reaction, a 0.05 M phosphoric acid buffer aqueous solution (pH 8.0) was employed, which is the same in the subsequent examples), introduced at a flow rate of 50 ml/hr (SV≈0.5 $hr^{-1}$) into the column from the top thereof, and a part of the remainder of the effluent was continuously obtained at 10 ml/hr.

The temperature in the column was continuously controlled at 10° C. by sending cold water through the jacket.

After continuing the reaction for 1,000 hours, the acrylamide concentration in the effluent was 10%, almost no unreacted acrylamide and by-products were detected, and the yield of acrylamide was nearly 100%.

EXAMPLE 2

Two jacketed columns (Nos. 1 and 2), each having an inner diameter of 3 cm and a length of 25 cm and being charged with 40 g of an immobilized microorganism which had been prepared in the same manner as in Example 1, were connected in series.

A feed mixture of 0.075 part of acrylonitrile and 0.925 part of a 0.05 M phosphoric acid buffer aqueous solution (pH 8.0) was, after being mixed with 4 parts of an effluent from the bottom of Column No. 1, introduced at a flow rate of 200 ml/hr (SV≈2 $hr^{-1}$), into Column No. 1 from the top thereof. A part of the remainder of the effluent from the bottom of Column No. 1 was flowed at a flow rate of 40 ml/hr (SV≈0.4 $hr^{-1}$) in Column No. 2 from the top thereof.

The temperature in the column was controlled at 10° C. by sending cold water through the jacket.

After continuing the reaction for 1,000 hours, the concentrations of acrylamide and unreacted acrylonitrile in the effluent from the bottom of Column No. 1 was 9.5% and 0.37%, respectively, the concentration of acrylamide in the effluent from the bottom of Column No. 2 was 10% and almost no unreacted acrylonitrile and by-products were detected therein, and the yield of acrylamide was nearly 100%.

EXAMPLE 3

Two jacketed columns (Nos. 1 and 2), each having an inner diameter of 3 cm and a length of 25 cm and being charged with 40 g of an immobilized microorganism which had been prepared in the same manner as in Example 1, were connected in series.

A feed mixture of 0.075 part of acrylonitrile and 0.925 part of a 0.05 M phosphoric acid buffer aqueous solution (pH 8.0) was, after being mixed with a part of an effluent from the bottom of Column No. 1, introduced at a flow rate of 80 ml/hr ($SV \approx 0.8$ $hr^{-1}$) into Column No. 1 from the top thereof. A part of the remainder of the effluent from the bottom of Column No. 1 was flowed at a flow rate of 40 ml/hr ($SV \approx 0.4$ $hr^{-1}$) in Column No. 2 from the top thereof.

The temperature in the column was controlled at 10° C. by sending cold water through the jacket.

After continuing the reaction for 1,000 hours, the concentration of acrylamide in the effluent from the bottom of Column No. 2 was 10% and almost no unreacted acrylonitrile and by-products were detected.

EXAMPLE 4

Two jacketed columns (Nos. 1 and 2), each having an inner diameter of 3 cm and a length of 25 cm and being charged with 40 g of an immobilized microorganism which had been prepared in the same manner as in Example 1, were connected in series. A feed mixture of 0.075 part of acrylonitrile and 0.925 part of a 0.05 M phosphoric acid buffer aqueous solution (pH 8.0) was, after being mixed with 9 parts of an effluent from the bottom of Column No. 1, introduced at a flow rate of 400 ml/hr ($SV \approx 4$ $hr^{-1}$) into Column No. 1 from the top thereof. A part of the remainder of the effluent from the bottom of Column No. 1 was flowed at a flow rate of 40 ml/hr ($SV \approx 0.4$ $hr^{-1}$) in Column No. 2 from the top thereof.

The temperature in the column was controlled at 10° C. by sending cold water through the jacket.

After continuing the reaction for 1,000 hours, the concentration of acrylamide in the effluent from the bottom of Column No. 2 was 10% and almost no unreacted acrylonitrile and by-products were detected.

EXAMPLE 5

The procedure of Example 1 was repeated except that a feed mixture of 0.079 parts of methacrylonitrile and 0.921 part of a 0.05 M phosphoric acid buffer aqueous solution (pH 8.0) was used in place of the feed mixture of 0.075 part of acrylonitrile and 0.925 part of the 0.05 M phosphoric acid buffer aqueous solution (pH 8.0).

After continuing the reaction for 1,000 hours, the concentration of methacrylamide in the effluent was 10%, almost no unreacted methacrylonitrile and by-products were detected, and the yield of methacrylamide was nearly 100%.

EXAMPLE 6

Three jacketed columns (Nos. 1, 2 and 3), each having an inner diameter of 3 cm and a length of 25 cm and being charged with 40 g of an immobilized microorganism which had been prepared in the same manner as in Example 1, were connected in series. A feed mixture of 0.075 part of acrylonitrile and 0.925 part of a 0.05 M phosphoric acid buffer aqueous solution (pH 8.0) was, after being mixed with 4 parts of an effluent from the top of Column No. 2, introduced into Column No. 1 upward from the bottom thereof at a flow rate of 200 ml/hr$^{-1}$ ($SV \approx 2$ $hr^{-1}$). An effluent from the top of Column No. 1 was all flowed in Column No. 2 upward from the bottom thereof. A part of the remainder of the effluent from the top of Column No. 2 was flowed in Column No. 3 upward from the bottom thereof at a flow rate of 40 ml/hr ($SV \approx 0.4$ $hr^{-1}$) and an effluent was continuously withdrawn from the top thereof.

The temperature in the column was controlled at 10° C. as in Example 1.

After continuing the reaction for 1,000 hours, the concentration of acrylamide in the effluent from the top of Column No. 1 was 10% and almost no unreacted acrylonitrile and by-products were detected.

EXAMPLE 7

A dispersion of a washed mass (water content 75%) of Strain N-774, which had been prepared by aerobically incubating on a culture medium (pH 7.2) containing 1% of glucose, 0.5% of peptone, 0.3% of yeast extract and 0.3% of malt extract, was irradiated with ultrasonic waves to extract enzyme therefrom. The treatment with ultrasonic waves was carried out by irradiating the 0.05 M phosphate buffer solution containing the microorganisms in the concentration of 5% with ultrasonic waves of 20 KHz at a temperature of 4° C. for 20 minutes. The irradiation apparatus used was Sonifier W-185 type (Branson Sonic Power Comp.). The thus extracted enzyme was mixed with porous strong basic anion exchange resin Amberlite 904 (produced by Rohm & Haas Co.), stirred at about 10° C. for 6 hours, and deposited on and bonded to the anion exchange resin. Thereafter the solution was separated to provide an immobilized enzyme.

Two jacketed columns (Nos. 1 and 2), each having an inner diameter of 3 cm and a length of 25 cm and being charged with 100 ml of the immobilized enzyme, were connected in series. A feed mixture of 0.075 part of acrylonitrile and 0.925 part of pure water was, after being mixed with 4 parts of an effluent from the bottom of Column No. 1 (pure water at the start of the reaction), introduced at a flow rate of 300 ml/hr ($SV \approx 3$ $hr^{-1}$) into Column No. 1 from the top thereof. A part of the remainder of the effluent from the bottom of Column No. 1 was flowed in Column No. 2 from the top thereof at a flow rate of 60 ml/hr ($SV \approx 0.6$ $hr^{-1}$).

The temperature in the column was controlled at 10° C.

After continuing the reaction for 200 hours, the concentration of acrylamide in the effluent from the bottom of Column No. 2 was 10% and almost no unreacted acrylonitrile and by-products were detected.

COMPARATIVE EXAMPLE

Tow jacketed columns (Nos. 1 and 2), each having an inner diameter of 3 cm and a length of 25 cm and being charged with 40 g of an immobilized microorganism which had been prepared in the same manner as in Example 1, were connected in series. A feed mixture of 0.075 part of acrylonitrile and 0.925 part of a 0.05 M phosphoric acid buffer aqueous solution (pH 8.0) was introduced into Column No. 1 from the top thereof at a flow rate of 40 ml/hr (SV ≈0.4 hr$^{-1}$). An effluent from the bottom of Column No. 1 was introduced into Column No. 2 at the top thereof at the same flow rate as above (i.e., 40 ml/hr).

The temperature in the column was controlled at 10° C.

On continuing the reaction for 50 hours, the concentration of unreacted acrylonitrile in an effluent from the bottom of Column No. 2 increased, reaching 1,000 ppm. At this time, the concentration of acrylamide was 9.9%. On further continuing the reaction for several hours, the concentration of acrylonitrile from the bottom of Column No. 2 abruptly increased and it became materially impossible to further continue the reaction.

While the invention has been described in detail and with reference to specific embodiments thereof, it will be apparent to one skilled in the art that various changes and modifications can be made therein without departing from the spirit and scope thereof.

What is claimed is:

1. A process for continuously producing acrylamide or methacrylamide from acrylonitrile or methacrylonitrile by use of a microorganism capable of promoting the hydration reaction of acrylonitrile or methacrylonitrile into the corresponding amide compound, said process comprising immobilizing the microorganism or enzyme extracted therefrom, continuously bringing the acrylonitrile or methacrylonitrile into contact with the immobilized microorganism or enzyme in at least one reactor containing an aqueous medium at a pH of 6 to 10 to cause the hydration reaction in a reaction solution, and recycling a part of the reaction solution to dilute the unreacted acrylonitrile or methacrylonitrile and water therewith in a ratio of 2 to 100 parts by volume of reaction solution to the volume of acrylonitrile or methacrylonitrile and aqueous medium used to produce said reaction solution.

2. A process as in claim 1 wherein the reactor is a fixed bed type or a fluidized bed type reactor.

3. A process as in claim 1 wherein the reactor is a fixed bed type.

4. A process as in claim 1 wherein the SV value of each reactor is 0.1 to 20 (hr$^{-1}$).

5. A process as in claim 1 wherein the SV value of each reactor is 0.3 to 5 (hr$^{-1}$).

6. A process as in claim 1 wherein the microorganism is immobilized with a polyacrylamide based gel.

7. A process as in claim 1 wherein the concentration of acrylamide or methacrylamide in the reaction solution is in a range of from about 5 to 25% by weight.

8. A process as in claim 1 wherein the reaction temperature is from the freezing point of the reaction solution to about 30° C.

9. A process as in claim 1 wherein the reaction temperature is from the freezing point of the reaction solution to 15° C.

10. A process as in claim 1 wherein the microorganism is selected from the genera Bacillus, Bacteridium, Micrococcus, Brevibacterium, Corynebacterium and Nocardia.

11. A process as in claim 1 wherein the microorganism is selected from the genera Corynebacterium and Nocardia.

12. A process as in claim 12, wherein the microorganism is selected from the group consisting of Strain N-771, Strain N-774, and Strain N-775.

13. A process as in claim 1 wherein the immobilizing of the microorganism or enzyme extracted therefrom is carried out at a temperature of 15° C. or less.

14. A process as in claim 1 wherein the pH is maintained from 7 to 9.

* * * * *